(12) United States Patent
Shirley et al.

(10) Patent No.: US 8,672,919 B2
(45) Date of Patent: Mar. 18, 2014

(54) DUAL BALLOON CATHETER ASSEMBLY

(75) Inventors: Gary Bradford Shirley, Bloomington, IN (US); William F. Moore, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 838 days.

(21) Appl. No.: 12/233,349

(22) Filed: Sep. 18, 2008

(65) Prior Publication Data
US 2010/0069900 A1 Mar. 18, 2010

(51) Int. Cl.
*A61M 31/00* (2006.01)

(52) U.S. Cl.
USPC .......................................... 604/509; 606/21

(58) Field of Classification Search
USPC ........ 606/20–23, 26, 192–193; 607/104, 105; 604/96.01–103.14, 500–522
See application file for complete search history.

(56) References Cited

U.S. PATENT DOCUMENTS

| | | | |
|---|---|---|---|
| 4,994,033 A * | 2/1991 | Shockey et al. | 604/101.02 |
| 5,242,397 A | 9/1993 | Barath et al. | |
| 5,514,092 A | 5/1996 | Forman et al. | |
| 6,428,534 B1 * | 8/2002 | Joye et al. | 606/21 |
| 6,811,550 B2 | 11/2004 | Holland et al. | |
| 6,939,320 B2 * | 9/2005 | Lennox | 604/103.02 |
| 6,955,174 B2 | 10/2005 | Joye et al. | |
| 7,081,112 B2 | 7/2006 | Joye et al. | |
| 2004/0260328 A1 | 12/2004 | Zvuloni et al. | |
| 2005/0288632 A1 | 12/2005 | Willard | |
| 2006/0015092 A1 | 1/2006 | Joye et al. | |
| 2006/0212028 A1 | 9/2006 | Joye et al. | |
| 2006/0224115 A1 | 10/2006 | Willard | |

* cited by examiner

*Primary Examiner* — Kevin C. Sirmons
*Assistant Examiner* — Phillip Gray
(74) *Attorney, Agent, or Firm* — Brinks Gilson & Lione; John C. Bacoch

(57) ABSTRACT

A dual balloon catheter assembly and method of use thereof are provided. The dual balloon catheter assembly may be used in a cryoplasty treatment that is provided in combination with eluting an antiproliferative to reduce and/or eliminate vessel fractures, thereby inhibiting proliferative response after angioplasty.

9 Claims, 4 Drawing Sheets

DUAL BALLOON CATHETER ASSEMBLY

BACKGROUND

The present invention relates generally to medical devices and more particularly to balloon catheters used to dilate narrowed portions of a lumen.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, coronary angioplasty using a balloon catheter has drawn particular attention from the medical community because of the growing number of people suffering from heart problems associated with stenosis. This has lead to an increased demand for medical procedures to treat such problems. The widespread frequency of heart problems may be due to a number of societal changes, including the tendency of people to exercise less while eating greater quantities of unhealthy foods, in conjunction with the fact that people generally now have longer life spans than previous generations. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the coronary artery to be treated. During this stage, the balloon is uninflated and collapsed onto the shaft of the catheter in order to present a low profile which may be passed through the arterial lumens. Once the balloon is positioned at the narrowed part of the artery, the balloon is expanded by pumping an inflation solution through the catheter to the balloon. As a result, the balloon presses against the inner wall of the artery to dilate it. Typical inflated pressures of the balloon may range between about 6 atm to about 20 atm (i.e, 90 psi-300 psi). If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the body. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed coronary arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters.

Although the inventions described below may be useful in treating hardened regions of stenosis, the claimed inventions may also solve other problems as well.

SUMMARY

The invention may include any of the following aspects in various combinations and may also include any other aspect described below in the written description or in the attached drawings.

In a first aspect, a double balloon catheter assembly for dilation of a vessel wall is provided. The assembly comprises a non-porous inner balloon having a proximal portion, a distal portion, and an outer surface extending between the proximal and the distal portions. At least a portion of the outer surface of the inner balloon is pre-coated with therapeutic agent so as to be subsequently entrained by a fluid. The outer balloon is radially spaced apart from the inner balloon by an annular lumen. The outer balloon comprises pores in fluid communication with the annular lumen. The pores are sized to pass the therapeutic agent therethrough. A shaft is also provided having a distal end and a proximal end. The inner and the outer balloons are mounted on the distal end of the shaft. The shaft comprises an inflation lumen extending therethrough in fluid communication with an interior region of the inner balloon to expand the inner balloon between a deflated state and an inflated state.

In a second aspect, a method for treating a stenosed vessel wall is provided. A balloon catheter assembly is provided comprising a non-porous inner balloon, the inner balloon having an outer surface wherein at least a portion of the outer surface is pre-coated with a therapeutic agent. The assembly further comprises an outer balloon disposed over the inner balloon, the outer balloon being spaced apart from the inner balloon by an annular lumen. The outer balloon has a porous structure. Fluid is introduced into the annular lumen. The inner balloon is inflated so as to push out the outer balloon against the stenosed vessel wall. Therapeutic agent is eluted with the fluid through the pores of the outer surface of the outer balloon and into the vessel wall.

In a third aspect, a double cryoplasty balloon catheter assembly for dilation of a vessel wall is provided. A non-porous inner balloon is provided having a proximal portion and a distal portion. The inner balloon is configured to receive a predetermined amount of cryogenic coolant sufficient to cool the inner balloon to a temperature adapted to induce apoptosis. The assembly further comprises an outer balloon disposed over the inner balloon. The outer balloon is radially spaced apart from the inner balloon by an annular lumen. The outer balloon comprises pores in fluid communication with the annular lumen. A shaft having a distal end and a proximal end is provided for mounting the inner and the outer balloons along the distal end of the shaft. The shaft comprises an inflation lumen extending therethrough in fluid communication with an interior region of the inner balloon to expand the inner balloon between a deflated state and an inflated state.

In a fourth aspect, a method for treating a stenosed vessel wall is provided. A balloon catheter assembly is provided comprising an inner balloon. The inner balloon has an outer surface wherein at least a portion of the outer surface is coated with an antiproliferative. The assembly further comprising an outer balloon disposed over the inner balloon, in which the outer balloon is spaced apart from the inner balloon by an annular lumen. The outer balloon has a porous structure. A cryogenic pressurized flow of coolant is introduced from a supply of cryogenic coolant into the inner balloon. A flow of fluid is introduced through the annular lumen. The inner balloon is inflated so as to push out the outer balloon against the stenosed vessel wall. The interior volume of the inner balloon is cooled to a temperature sufficient to induce apoptosis of the stenosed vessel wall. An antiproliferative is eluted with the fluid through the pores of the outer surface of the balloon into the vessel wall.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
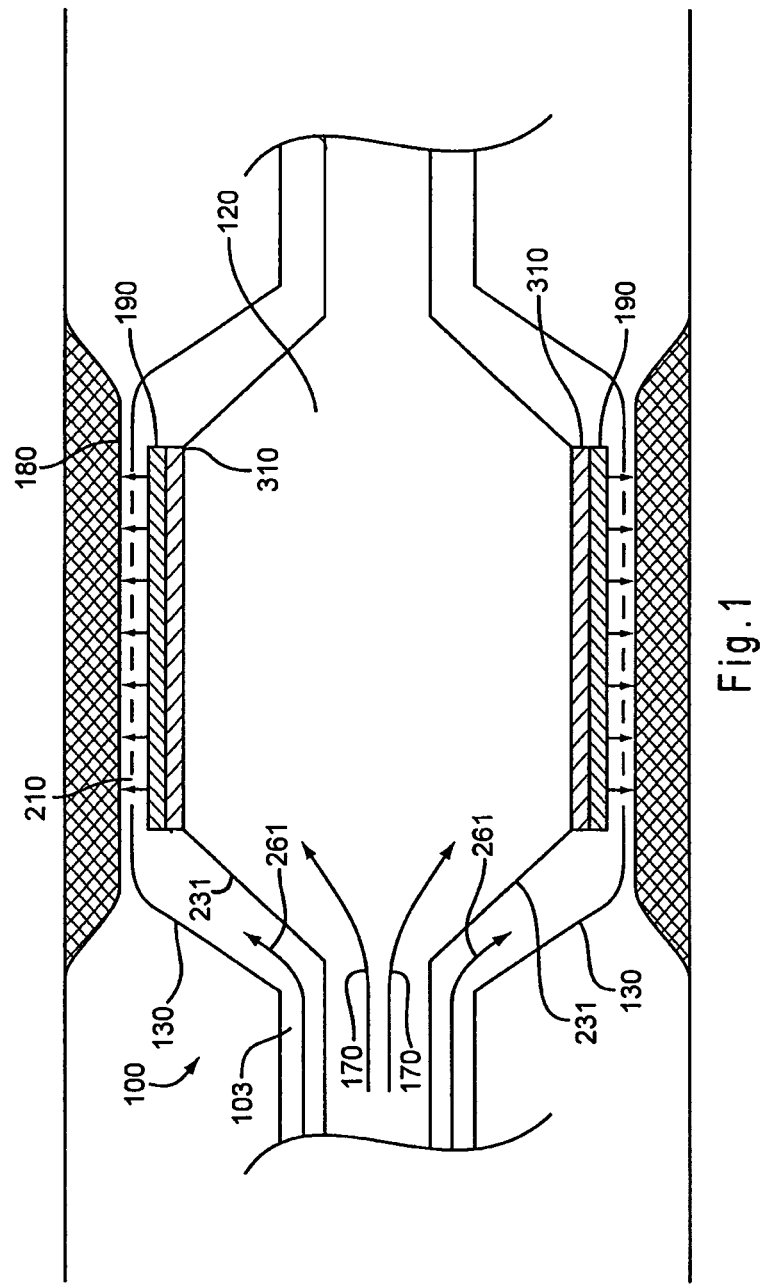
FIG. 1 shows an exemplary dual balloon assembly.
Figure 2:
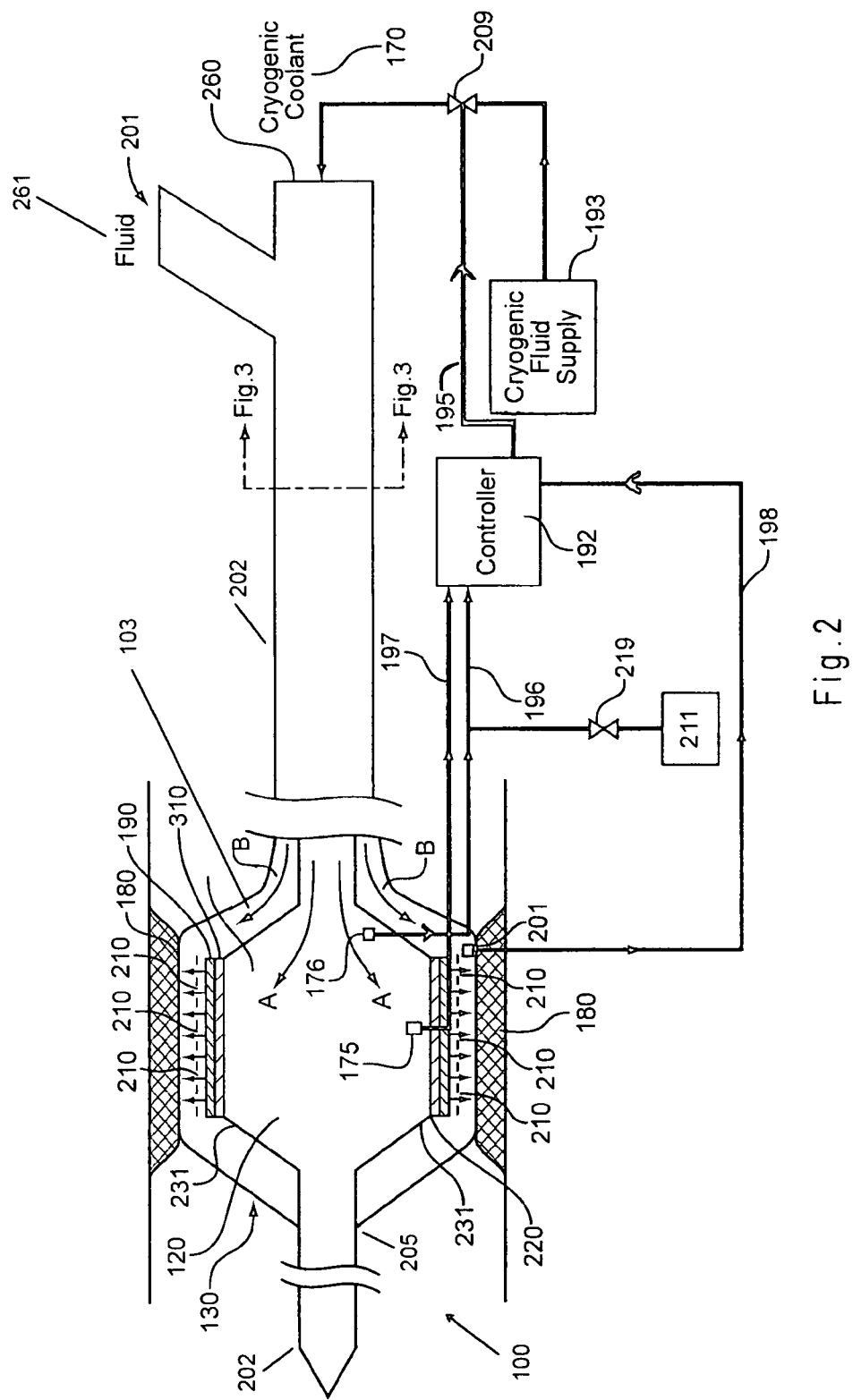
FIG. 2 shows the dual balloon assembly of FIG. 1 being utilized in a cryoplasty procedure.

An exemplary dual balloon assembly 100 is shown in FIGS. 1 and 2. The dual balloon assembly 100 includes an inner inflation balloon 120 and a perforated outer balloon 130. The perforated outer balloon 130 is radially disposed around the inner inflation balloon 120. The inner balloon 120 is in fluid communication with inflation port 260 (FIG. 2) through the body of catheter shaft 202. The outer balloon 130 is in fluid communication with inflation port 201 through the catheter shaft 202. An annular lumen 103 (FIGS. 1 and 2) for receiving fluid 261 (e.g., saline) from inflation port 201 is formed between the inner inflation balloon 120 and the perforated outer balloon 130. The annular lumen 103 is in fluid communication with pores 210 extending along at least a portion of outer balloon 130. The pores 210 allow material (e.g., fluid and therapeutic agents 190 contained within the fluid) to pass therethrough. The inner balloon 120 and outer balloon 130 may be sealed to the distal end 205 of catheter shaft 202.

The dual balloon assembly 100 may be used for various applications, including delivery of a therapeutic agent 190 locally to tissue while simultaneously dilating a body vessel through pores 210 of the outer balloon 130. One example includes delivery of a therapeutic agent 190 to a dilated portion of a coronary artery in a PTCA procedure. In particular, the inner balloon 120 may be inflated to a desired diameter in a body vessel such as a coronary artery by injecting a suitable inflation fluid, such as pressurized air, gas, or liquid through the inflation port 260. The inner balloon 120 may be inflated until the outer balloon 130 contacts a portion of the body vessel wall at a point of treatment. A fluid 261 containing a therapeutic agent 190 and/or a diagnostic agent (e.g., fluoroscopic contrast media) may be injected through the injection port 201, transported within the catheter shaft 202, and introduced through annular lumen 103 between the outer balloon 130 and the inner balloon 120. The therapeutic agent may be pressurized to deliver the agent through the wall of a body vessel through the pores 210 in the outer balloon 130 before, during, or after inflation of the inner balloon 120. Preferably, the therapeutic agent is eluted through the pores 210 before complete inflation of inner balloon 120.

Other applications utilizing the dual balloon assembly 100 are also contemplated. In a preferred embodiment, the dual balloon assembly 100 is used in a cryoplasty procedure in which the inner balloon 120 functions as a cryoplasty balloon. At least a portion of the outer surface 231 of the inner balloon 120 may be loaded with an antiproliferative 190. Preferably, the antiproliferative is paclitaxel. FIGS. 1 and 2 show a layer of antiproliferative 190 coated along a working diameter of the outer surface 231 of the inner balloon 120. Alternatively, the entire outer surface 231 of inner balloon 120 may be coated with the antiproliferative 190.

Figure 3:
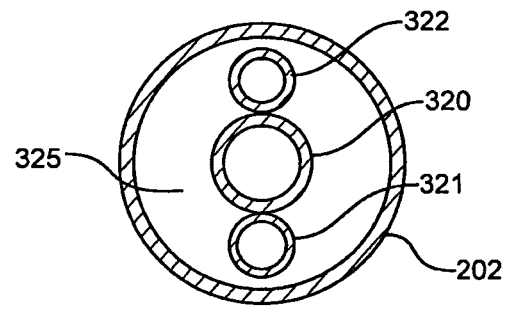
FIG. 3 is a cross-sectional view of the dual balloon assembly of FIG. 1 taken along line 3-3 of catheter shaft.

In cryoplasty operation, the balloon catheter assembly 100 is initially delivered to a stenosed vessel region 180. The assembly 100 preferably is configured to receive a wire guide through wire guide lumen 320 (FIG. 3). The assembly 100 is advanced along the wire guide. Having reached the stenosed vessel region 180, the cryoplasty procedure may ensue. The cryogenic coolant 170 may be introduced from a fluid supply source such as a canister 193 (FIG. 2), which contains the coolant 170 in the form of a high pressure liquid. Suitable cryogenic coolants are non-toxic and are usually in the form of a liquid refrigerant or liquid/gas mixture within canister 193. The cryogenic coolant 170 as contained in the canister 193 may include liquid nitrous oxide, liquid saline, liquid nitrogen, liquid carbon dioxide, and the like. In one example, the canister 193 comprises high pressure liquefied nitrous oxide at a saturation pressure of about 500 psi and at a saturation temperature of about 0° C.

A control valve 209 opens for a time sufficient to introduce a predetermined amount of cryogenic coolant 170 as a saturated liquid into port 260. The valve 209 may be open for less than a second to introduce cryogenic coolant 170 into the proximal port 260 of the balloon catheter 100 (FIG. 2). In this example, the coolant 170 is liquefied nitrous oxide. The liquefied nitrous oxide coolant 170 emerges from canister 193 at aboutb 500 psi and about 0° C. The coolant 170 travels along catheter shaft 202 within a coolant lumen 322 (FIG. 3) of shaft 202. Some of the coolant 170 may flash vaporize from liquid to gas as it travels along the catheter shaft 202. As the coolant 170 enters the interior of the inner balloon 120, as indicated by arrows "A" in FIG. 2, the coolant 170 experiences a reduction in pressure in which at least a portion of the liquid coolant 170 flashes into vapor. Both the vapor and any residual liquid of coolant 170 are cooled to the saturation temperature of the coolant 170 along the saturation curve for nitrous oxide, in the direction of the arrow shown in FIG. 5. The cryogenic coolant 170 flows into the interior of inner balloon 120 and cools the interior of the inner balloon 120 and outer surface 231 of inner balloon 120. This infusion of a predetermined amount of cryogenic coolant 170 into inner balloon 120 simultaneously cools and partially inflates the inner balloon 120. A predetermined amount of time (e.g., 10-25 seconds) may be allowed to transpire before a temperature reading may be sensed by temperature sensor 175, which is shown affixed to an outer surface 231 of inner balloon 120 in FIG. 2. The temperature sensor 175 transmits a temperature electrical signal 197 (FIGS. 2 and 4) to controller 192. Controller 192 may function to initiate, monitor, and control cooling of the target tissue at stenosed region 180 (FIG. 1).

Figure 4:
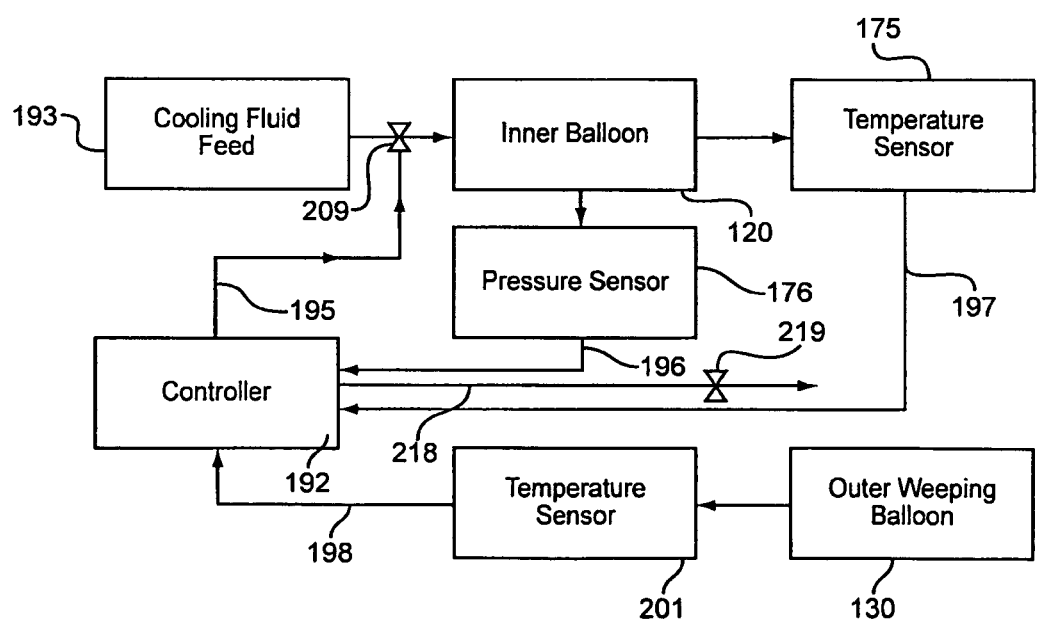
FIG. 4 shows components of a feedback control system for regulating, initiating, and ceasing the supply of cryogenic coolant.

Referring to FIGS. 2 and 4, the controller 192 reads the temperature measurement provided by temperature sensor 175 via electrical signal 197. The controller 192 evaluates whether additional coolant 170 is required to be fed into inner balloon 120 from the canister 193 and then sends the appropriate electric signal 195 to the control valve 209 for cryogenic fluid supply canister 193 (i.e., cooling fluid supply feed). If additional coolant 170 is determined necessary by controller 192, the signal 195 causes control valve 209 to open from its closed position for a predetermined amount of time (e.g., about 1 second) to allow a predetermined amount of coolant 170 to be introduced through port 260 of the catheter shaft 202. The control valve 209 continues to open and close until the desired cooling and inflation pressure have occurred within inner and outer balloons 120 and 130. The opening and subsequent closing of control valve 209 to introduce a predetermined amount of coolant 170 constitutes a "cycle." Generally, multiple cooling "cycles" may be required to reach the desired pressure level (e.g., 8-10 atm) and cooling temperature (e.g., about −5° C.-10° C.) within inner balloon 120. As a result, the controller 192 may regulate the flow of coolant 170 in a cycled manner based on temperature measurements.

Temperature measurements of the outer balloon 130 may also be provided by temperature sensor 201. The controller 192 may then regulate flow of coolant 170 based on a temperature electrical signal 198 (FIGS. 2 and 4) that is transmitted from temperature sensor 201.

Alternatively or in addition to the above described temperature measurements, the regulation of flow of coolant 170 may be based on pressure measurements. Pressure sensor 176 is shown affixed to an interior surface of inner balloon 120 as shown in FIG. 2. The pressure sensor 176 transmits a pressure electrical signal 196 to controller 192 (FIGS. 2 and 4). The controller 192 reads the pressure measurement provided by pressure sensor 176 and then evaluates whether additional coolant 170 is required to be fed to inner balloon 120 from the canister 193. If additional coolant 170 is determined necessary by controller 192, control valve 209 opens from its closed position for a predetermined amount of time (e.g., about 1 second) to allow a predetermined amount of coolant 170 to be introduced through port 260 of the catheter shaft 202. The time at which the control valve 209 opens and closes and the duration for keeping the control valve 209 opened and closed is determined by controller 192. In one example, the inner balloon 120 may reach a fully inflated state in a time from about 0.2 seconds to about 20 seconds after introduction of the coolant 170 into shaft 202.

The inner balloon 120 pressure may be further controlled by a pressure relief valve 219 shown in FIGS. 2 and 4. Similar to control valve 209, the pressure relief valve 219 is in electrical communication with controller 192. Excess pressure within balloon 120 may be relieved through exhaust lumen 325 (FIG. 3). FIG. 3 shows that the exhaust lumen 325 is preferably larger relative to the other lumens 320, 321, and 322 in order to be capable of exhausting a large volume of coolant 170 gas relatively quickly. Excess pressure may be detected by pressure sensor 176 (FIG. 1) via pressure electrical signal 196. Controller receives signal 196 and then transmits pressure relief electrical signal 218 (FIG. 4) to pressure relief valve 219. Signal 218 causes valve 219 to open for a predetermined amount of time to enable excess coolant 170 gas to be relieved into enclosed container 211 (FIG. 2).

Figure 5:
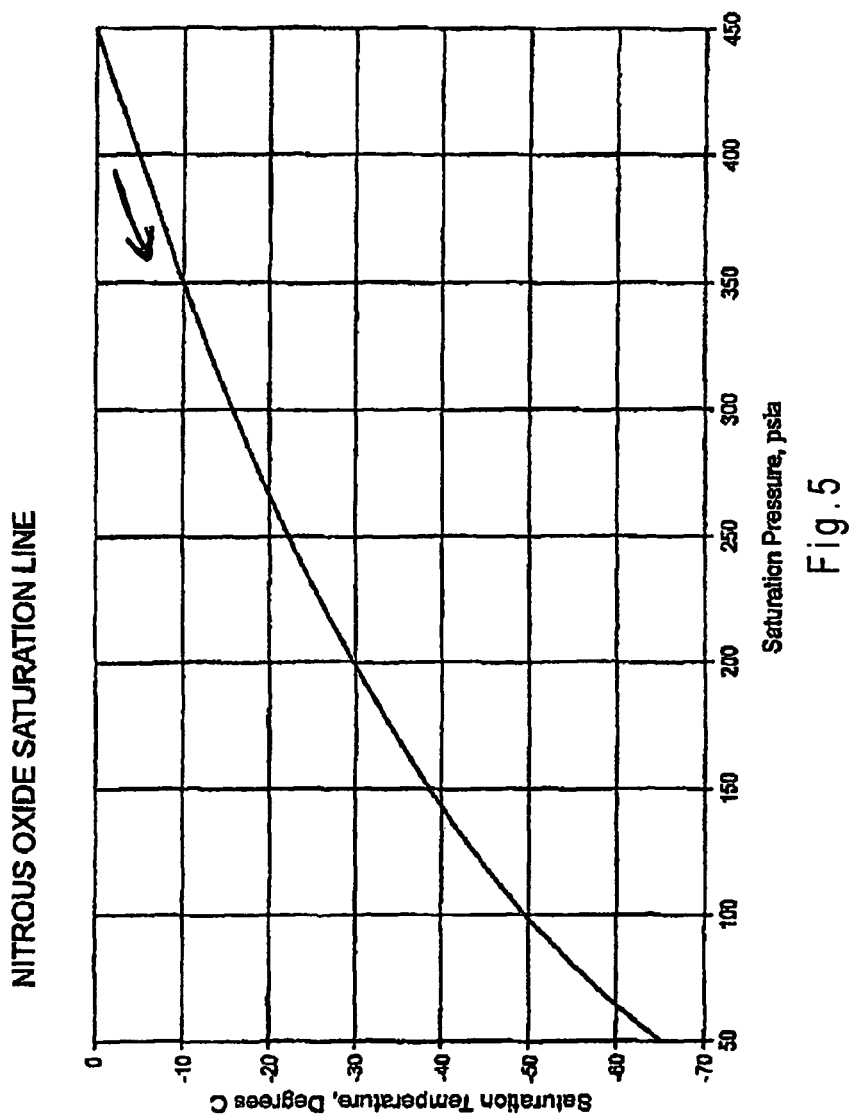
FIG. 5 shows a saturated liquid-vapor curve for nitrous oxide.

As can be seen from FIG. 5, the type of cryogenic coolant governs the resultant cooling and inflation pressures within inner balloon 120. FIG. 5 is a liquid-vapor saturation curve for a nitrous oxide cryogenic coolant. At 100 psia (i.e., about 7 atm), which is within the range of typical operating pressure for angioplasty balloons, the temperature inside inner balloon 120 will be about −50° C. At 150 psia (about 10 atm), the temperature inside inner balloon 120 will be about −38° C. Taking into account the temperature difference between the inner balloon 120 and the target tissue, such inner balloon 120 temperatures may result in the appropriate cooling of the tissue surrounding stenosed vessel region 180 to about −5° C. to about −10° C. Preferably, the body tissue is cooled to a temperature from about −5° C. to about −15° C. to induce programmed cell death of the body tissue, otherwise known in the art as apoptosis. Other suitable coolants may have different liquid-vapor saturation curves which will result in a different pressure and temperature within inner balloon 120.

As the inner balloon 120 gradually expands as described above, the inner balloon 120 begins to press against outer balloon 130, thereby reducing the free space within the annular lumen 103. As the free space within annular lumen 103 compresses, the flow of fluid 261 may encounter increased resistance such that elution of entrained antiproliferative 190 through the pores 210 may become increasingly difficult to achieve. Accordingly, prior to complete inflation of inner balloon 120, it is preferable to begin the process of injecting fluid 261 through annular lumen 103. A fluid 261 is injected at port 201 and thereafter along catheter shaft 202 within lumen 321 (FIG. 3). Introduction of fluid 261 is preferably not designed to generate sufficient inflation pressure of outer balloon 130. The fluid 261 flows between the inner and outer balloons 120 and 130, as indicated by arrows "B". The fluid 261 contacts outer surface 231 of inner balloon 220. As the fluid 261 (FIG. 1) contacts outer surface 231, it entrains (i.e., picks up) the antiproliferative 190 and thereby functions as a liquid carrier for the antiproliferative 190. Fluid 261 may be any suitable fluid that is biocompatible with the particular antiproliferative 190 being used. In a preferred embodiment, the antiproliferative 190 being utilized is paclitaxel. The fluid 261 used for entraining the paclitaxel may include alcohol, ethanol, iodine contrast imaging agent, and saline. Other suitable fluids 261 for entraining paclitaxel include medical grade saline solution and various Cremophore solvents. Thereafter, the fluid 261 with entrained paclitaxel 190 flows out through pores 210 of the outer balloon 130 and into the stenosed region 180. The paclitaxel 190 may be applied to the outer surface 231 of the inner balloon 120 by coating. The paclitaxel 190 may be coated along the entire outer surface 231 of inner balloon 120 in a variety of effective dosage amounts, including about 3 μg per $mm^2$ of surface area of the outer surface 231. Between about 5 to about 10 cc of fluid 261 may be introduced through annular lumen 103 to entrain the paclitaxel 190 through pores 210 of the outer balloon 130.

As inner balloon 120 is expanding, it pushes out against the outer balloon 130 to cause the outer balloon 130 to expand towards the stenosed vessel wall 180. At a certain juncture in the cryoplasty procedure, coolant 170 and fluid 261 may be simultaneously introduced through their respective lumens 322 and 321 (FIG. 3) of catheter shaft 202. Preferably, after the fluid 261 with entrained paclitaxel 190 outflows into vessel 180 through pores 210, the outer surface of outer balloon 130 (FIG. 2) comes into direct contact with stenosed region 180 to cool the target tissue. Preferably, all of the paclitaxel 190 is eluted into the target tissue of the stenosed vessel 180 prior to the outer balloon 130 contacting the tissue surrounding the stenosed region 180. Alternatively, elution may occur after or simultaneously with cooling of tissue surrounding region 180.

After completion of the elution of paclitaxel 190 and the cooling of tissue by dual balloon assembly 100, fluid flow 261 and coolant flow 170 may cease. At this juncture, the coolant 170 gas within the inner balloon 120 is exhausted preferably by vacuum through exhaust lumen 325 (FIG. 3) of catheter shaft 202.

As described above, the combination of cryoplasty treatment with an antiproliferative 190 may reduce and/or eliminate vessel fractures, thereby inhibiting proliferative response after angioplasty procedures. The above procedure offers the advantage of the dual balloon assembly 100 being pre-coated with the antiproliferative 190. As a result, the practitioner need not be concerned about injecting the antiproliferative 190 at a predetermined drug delivery rate during the procedure.

Excessive cooling of the stenosed vessel wall 180 should be avoided because temperatures that are too cold may result in necrosis, a type of injury that yields cellular inflammation, cellular proliferation, and restenosis. Accordingly, the outer balloon 130 may be formed from a material that acts as a thermal insulator. FIGS. 1 and 2 show that a thermal barrier 310 may be disposed along at least a portion of the outer surface 231 of the inner balloon 120. Suitable thermal barriers 310 may include textiles (e.g., polyethylene) as are commonly used in the art to form vascular grafts. Other thermal barriers 310 may include polyethylene terepthalate (PET) or polyethylene napthlate (PEN) affixed to the outer surface 231 by adhesion bonding, heat welding, fasteners, or the like. FIG. 3 shows that the thermal barrier layer 310 is disposed between an outer surface 231 of inner balloon 120 and the antiproliferative layer 190. Still further, the thermal barrier 310 may comprise a sleeve that is wrapped around the outer surface 231 of inner balloon 120.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A method for treating a stenosed vessel wall, comprising the steps of:
   (a) delivering a balloon catheter assembly to a target region, the balloon catheter assembly comprising a catheter shaft having a first inflation port and a second inflation port, a non-porous inner balloon in fluid communication with the first inflation port, the inner balloon being uninflated and having an outer surface with at least a portion of the outer surface pre-coated with a therapeutic agent, the balloon catheter assembly further comprising an outer balloon in fluid communication with the second inflation port, the outer balloon disposed over the inner balloon and being uninflated and spaced apart from the inner balloon by an annular lumen, the outer balloon having a porous structure;
   (b) with the balloon catheter assembly delivered to the target region, introducing a first fluid into the first inflation port to inflate the inner balloon;
   (c) prior to completing the inflation of the inner balloon, introducing a second fluid into the second inflation port to entrain the therapeutic agent coated on the outer surface of the inner balloon;
   (d) eluting the therapeutic agent with the second fluid through the pores of the outer surface of the outer balloon porous structure.

2. The method of claim 1, wherein the outer balloon contacts the stenosed vessel wall after substantially all of the therapeutic agent with the second fluid has outflowed through the porous structure of the outer balloon.

3. The method of claim 1, wherein the second fluid is selected from the group consisting of alcohol, iodine contrast imaging agent, saline, and solvents.

4. A method for treating a stenosed vessel wall, comprising the steps of:
   (a) delivering a balloon catheter assembly to a target region, the balloon catheter assembly comprising a catheter shaft having a first inflation port and a second inflation port, a non-porous inner balloon in fluid communication with the first inflation port, the inner balloon being uninflated and having an outer surface wherein at least a portion of the outer surface pre-coated with an antiproliferative, the balloon catheter assembly further comprising an outer balloon in fluid communication with the second inflation port, the outer balloon disposed over the inner balloon and being uninflated and spaced apart from the inner balloon by an annular lumen, the outer balloon having a porous structure;
   (b) with the balloon catheter assembly delivered to the target region, introducing a cryogenic pressurized flow of coolant from a supply of cryogenic coolant into the inner balloon to inflate the inner balloon;
   (c) prior to completing the inflation of the inner balloon, introducing a second fluid into the second inflation port to entrain the antiproliferative coated on the outer surface of the inner balloon within the fluid;
   (d) cooling a portion of the stenosed vessel wall to a temperature sufficient to induce apoptosis of the stenosed vessel wall; and
   (e) eluting the antiproliferative with the fluid through the porous structure of the outer balloon into the vessel wall.

5. The method of claim 4, further comprising a step of
   (f) regulating the flow of coolant.

6. The method of claim 5, wherein step (f) further comprises a controller selectively opening and closing a control valve located downstream of the supply of cryogenic coolant.

7. The method of claim 4, further comprising a step of:
   (f) monitoring a temperature and/or pressure of the inner balloon.

8. The method of claim 4, further comprising a step of (f) exhausting coolant gas through an exhaust lumen of the shaft.

9. The method of claim 5, further comprising opening a pressure relief valve to relieve the excess coolant gas from the inner balloon.

* * * * *